United States Patent
Shan et al.

(10) Patent No.: US 7,195,783 B2
(45) Date of Patent: Mar. 27, 2007

(54) **HYPERICIN AND *HYPERICUM* EXTRACT: SPECIFIC T-TYPE CALCIUM CHANNEL BLOCKER, AND THEIR USE AS T-TYPE CALCIUM CHANNEL TARGETED THERAPEUTICS**

(75) Inventors: Jacqueline J. Shan, Edmonton (CA); Xi-Chen Wu, Edmonton (CA); Peter K. T. Pang, Edmonton (CA); Lei Ling, Edmonton (CA)

(73) Assignee: FX Life Sciences International GmbH, Zug (CH)

( * ) Notice: Subject to any disclaimer, the term of this patent is extended or adjusted under 35 U.S.C. 154(b) by 0 days.

(21) Appl. No.: 09/481,572

(22) Filed: Jan. 11, 2000

(65) Prior Publication Data

US 2003/0207940 A1    Nov. 6, 2003

Related U.S. Application Data

(63) Continuation-in-part of application No. PCT/US99/14132, filed on Jul. 9, 1999.

(51) Int. Cl.
*A01N 65/00* (2006.01)

(52) U.S. Cl. ..................................... 424/725

(58) Field of Classification Search .............. 424/195.1
See application file for complete search history.

(56) References Cited

U.S. PATENT DOCUMENTS

| | | | |
|---|---|---|---|
| 5,120,412 A | | 6/1992 | Mazur et al. |
| 5,288,485 A | * | 2/1994 | Kikuta et al. |
| 5,433,957 A | * | 7/1995 | Kikuta et al. |
| 5,514,714 A | * | 5/1996 | Meruelo et al. |
| 6,056,961 A | * | 5/2000 | Lavie et al. ............. 424/195.1 |
| 6,113,907 A | * | 9/2000 | Khwaja et al. |

FOREIGN PATENT DOCUMENTS

| | | | |
|---|---|---|---|
| BE | 654916 | * | 10/1964 |
| BE | 654914 | * | 8/1993 |
| DE | 1692045 | * | 5/1971 |
| DE | 197 00 788 A | | 7/1998 |
| EP | 0599 307 B1 | | 6/1994 |
| EP | 0847756 | * | 6/1998 |
| JP | 09227398 | * | 9/1997 |
| WO | WO 89/03213 A | | 4/1989 |
| WO | WO 94/27952 A | | 12/1994 |
| WO | WO 96/33012 A | | 10/1996 |
| WO | WO 97/13489 | | 4/1997 |
| WO | WO 98/27970 A | | 7/1998 |

OTHER PUBLICATIONS

Dorland's Illustrated medical Dictionary, 27th edition, 1988, p. 460.*
John S. James, "(ATN) Hypericum: Common Herb Shows Antiretroviral Activity", Aids Treatment News No. 063 (Aug. 26, 1988), 6 pgs.
L. Lee Coyne, Ph.D., St. John's Wort, Nature's Prozac (publication date unknown) 2 pgs.
Johnson, D. et al., "Effects of Hypericum Extract LI 160 Compared with Maprotiline on Resting EEG and Evoked Potentials in 24 Volunteers", J. Geriatr. Psychiatry Neurol. (1994), vol. 7, (Suppl. 1) pp. S44-S46.
Lehrl, S., "Psychometrische Messung der Leistungskapazität unter antidepressiver Therapie mit Johanniskraut-Extrakt", Nervenheilkunde (1991) vol. 10, pp. 313-315.
Linde, Klaus, et al. "St. John's wort for depression-an overview and meta-analysis of randomised clinical trials", BMJ (Aug. 3, 1996) vol. 313, pp. 253-258.
V. Schulz, "Klinische Studien mit Psycho-Phytopharmaka", Zeitschrift für Phytotherapie, vol. 18, (1997) pp. 141-154.
"Pflanzliche Arzneien Score im Hirnleistung", Pharmakotherapie für die Praxis, Fortschr. Med. 111, Jg. (1993) Nr. 6, p. 50.
"Nootropika: BGA verlangt Therapie-Verbund", Pharmakotherapie für die Praxis, Fortschr. Med. 112 Jg. (1994) Nr. 4, p. 48.
"St. John's Wort" from http://nutrifocus.com as of Feb. 10, 2004 (publication date unknown).
Noamesi et al., "Anticonvulsant Effect of Aqueous and Ethanol Extracts of Mareya spicata Against Pentylenetetrazole, Lidocaine, and Aminophylline Induced Convulsions in Mice", Planta Medica, 1991, vol. 57, Suppl. 1, p. A55, see second paragraph.

* cited by examiner

*Primary Examiner*—Michael Meller
(74) *Attorney, Agent, or Firm*—Rothwell Figg Ernst & Manbeck (57) ABSTRACT

Hypericin has been shown to specifically inhibited T-type calcium channel activity. *Hypericum* extract containing hypericin also inhibited T-type calcium channel activity. Moreover, other chemicals in *Hypericum* extract showed a synergistic effect to hypericin. In view of this, hypericin or hypericin-containing *Hypericum* extract can be used as T-channel blockers. *Hypericum* extract, extract of other species of the *Hypericum* genus, extract of other plants containing hypericin, hypericin, hypericin derivatives, hypericin analogs, such as pseudohypericin, and other *hypericum* extract constituents can be used as therapeutics targeted at T-type calcium channels for treatment of diseases associated with T-channel abnormality. Methods for administering hypericin and *hypericum* extract are disclosed.

16 Claims, 7 Drawing Sheets

HYPERICIN AND *HYPERICUM* EXTRACT: SPECIFIC T-TYPE CALCIUM CHANNEL BLOCKER, AND THEIR USE AS T-TYPE CALCIUM CHANNEL TARGETED THERAPEUTICS

This application is a continuation-in-part of International Application PCT/US99/14132, filed Jul. 9, 1999, and designating the United States, the disclosure of which is incorporated by reference.

FIELD OF THE INVENTION

This invention relates to *Hypericum perforatum*, extracts of *Hypericum perforatum*, compounds found in *Hypericum perforatum*, e.g. hypericin, and the derivatives and analogs of hypericin. One aspect of the present invention is the discovery that *Hypericum perforatum* (referred to as *Hypericum* herein after unless otherwise indicated), *Hypericum* extracts, certain compounds in *Hypericum*, including hypericin, pseudohypericin, hyperforin, ashyperforin, quercetin, quercitrin, isoquercitrin, hyperoside, rutin, amentoflavone and hyperin, hypericin derivatives and hypericin analogs can be used as therapeutics targeted at T-type calcium channels in various biological systems, such as cardiovascular system, central nervous system and endocrine system, to treat diseases treatable with T-type calcium blocking agents. The diseases treatable with T-type calcium blocking agents include depression, chronic heart failure, congestive heartfailure, ischaemc condition, arrhythmia, angina pectoris, hypertension, hypo- and hyperinsulinemia, diabete mellitus, hyperaldosteronemia, epilepsy, migraine headache, brain aging or neurodegenerative related diseases, such as Alzheimer's disease, and preterm labor.

BACKGROUND OF THE INVENTION

Hypericin is one of the chemical constituents from a perennial herbaceous plant, *Hypericum perforatum* or St. John's Wort. *Hypericum* is known to have medicinal properties since ancient times and it is widely used in phytotheraphy. *Hypericum* has been widely researched for its antidepressant and anti-viral properties. In addition to these properties, *Hypericum* has historically been used for a variety of neurological conditions, including anxiety, insomnia due to restlessness, irritability, neuralgia, trigeminal neuralgia, neuroses, migraine headaches, fibrositis, dyspepsia, and sciatica. *Hypericum* contains several compounds of biological interest, including naphthodianthrones, e.g. hypericin and pseudohypericin, phloroglucinols, e.g. hyperforin and ashyperforin, and a broad spectrum of flavonoids which are considered to be primarily responsible for *Hypericum's* activity. However, the lack of a clearly definable pharmacologic mechanism of *Hypericum* and its chemical components cause the failure of identifying the constituents most responsible for *Hypericum's* activity.

Clinical studies demonstrated that *Hypericum* is effective in treating mild depression. Animal studies also showed that *Hypericum* extract relieved depressant symptoms. It was reported that *Hypericum* extract resulted in a down-regulation of adrenergic receptors in the rat frontal cortex after subchronic treatment. Some reported that hypericin inhibited monoamine oxidase (MAO) activity in vitro, but others have failed to confirm this effect. Other proposed mechanisms involve effects on serotonin. At very high doses, *Hypericum* extract inhibited seretonin re-uptake although it is not known which chemical in the extract is responsible. Studies have shown that both hypericin and pseudohypericin inhibited a variety of virus. Hypericin has been reported to inhibit the growth of glioma cell lines in vitro and to be a potent inducer of glioma cell death due to inhibition of protein kinase C(PKC). Receptortyrosine kinase activity of epidermal growth factor has also been reported to be inhibited by hypericin. These later effects have been linked to both the antiviral and antineoplastic activity.

It is known (F. R. Buhler, *J. Hypertension* supplement 15(5):s3–7, 1997; B. Cremers et al., *J. Cardiovascular Pharmacology*, vol. 29(5), pp. 692–6, 1997) that T-type channels are involved in pacemaker activity, low-threshold calcium spikes, neuronal oscillations and resonance, and rebound burst firing. It was reported that Mibefradil, a selective T-channel blocker, induces peripheral and coranary vasodilation. There is no reflex sympathetic activation and no negative inotropic effect. It increases coronary blood flow without increasing oxygen consumption and causes a slight slowing of the heart rate, thereby inducing diastolic relaxation. The latter improves subendocardial and small artery perfusion. Ventricular ectopic activity is reduced with mibefradil. The renin-angiotensin-aldosterone system and endothelin effects are blunted by T-channel inhibition. It is believed that mibefradil could lead to a greater therapeutic index and greater safety over conventional non-selective or L-type calcium channel blockers in the treatment of cardiovascular diseases. Mibefradil has been used to treat hypertension and angina clinically. It was reported that Zonisamide, a antiepileptic drug reduces T-type calcium current (M. Kito et al., *Seizure*, vol. 5(2), pp. 115–9, 1996). T-type calcium channels also facilitate insulin secretion by enhancing the general excitability of these cells. Therefore, T-type calcium channels may be therapeutic targets in hypo- and hyperinsulinemia (A. Bhaftacharjee et al., *Endocrinology*, vol. 138(9), pp. 3735–40, 1997). A direct link between T-type calcium channel activity and steroidogenesis has been suggested (M. F. Rossier et al., 1996).

SUMMARY OF THE INVENTION

Consequently, T-type calcium channel blockers, such as *Hypericum*, *Hypericum* extracts, extracts of species (e.g. *H. majus, H. formosum, H. calycinum, H. X moseranum, H. irazuense, H. reductum, H. patulum, H. mutilum, H. cruxandreae, H. hypericoides, H. densiflorum, H. prolificum, H. frondosum, H. cumilicola, H. anagalloides, H. androsaemum, H. tetrapterum, H. hirsutum, H. olympicum, H. hyssopifolium, H. elongatum* and *H. erratum*) of the *Hypericum* genus other than *Hypericum perforatum*, *Hypericum* constituents, including hypericin, pseudohypericin, hyperforin, ashyperforin, quercetin, quercitrin, isoquercitrin, hyperoside, rutin, amentoflavone and hyperin, hypericin derivatives and hypericin analogs of the present invention are effective in treating disorders characterized by an insufficiency of a steroid hormone.

Specific T-Channel inhibitory effect of hypericin and *Hypericum* extract containing 0.3% of hypericin have been found by the present inventors. The present inventors have unexpectedly found that hypericin and *Hypericum* extracts act as specific T-calcium channel blockers. In view of this, *Hypericum*, *Hypericum* extracts, extracts of species (e.g. *H. majus, H. formosum, H. calycinum, H. X moseranum, H. irazuense, H. reductum, H. patulum, H. mutilum, H. cruxandreae, H. hypericoides, H. densiflorum, H. prolificum, H. frondosum, H. cumilicola, H. anagalloides, H. androsaemum, H. tetrapterum, H. hirsutum, H. olympicum, H. hyssopifolium, H. elongatum* and *H. erratum*) of the *Hypericum* genus other than *Hypericum perforatum*, extracts of other plants containing hypericin, constituents of *Hypericum*, including hypericin, hypericin derivatives and hypericin analogs according to the present invention are expected to be useful for treating T-calcium channel targeted diseases such as arrthymia, coronary diseases, angina, hypertension, migraine, diabetes and preterm labor, etc.

Within the scope of the present invention are processes of using *Hypericum*; *Hypericum* extracts; extracts of species of the *Hypericum* genus other than *Hypericum perforatum*; *Hypericum* constituents, including hypericin, pseudohypericin, hyperforin, ashyperforin, quercetin, quercitrin, isoquercitrin, hyperoside, rutin, amentoflavone and hyperin; hypericin derivatives; or hypericin analogs to treat health disorders related to T-type calcium channels or treatable with T-calcium channel blockers in animals, including humans. The health disorders related to T-type calcium channels or treatable with T-type calcium blocking agents include depression, chronic heart failure, congestive heart failure, ischaemc condition, arrhythmia, angina pectoris, hypertension, hypo- and hyperinsulinemia, diabete mellitus, hyperaldosteronemia, epilepsy, migraine headache, brain aging or neurodegenerative related diseases, such as Alzheimer's disease, and preterm labor.

DETAILED DESCRIPTION OF THE INVENTION

The present inventors have found that a commercially available standardized *Hypericum* extract containing the primary compounds, such as hypericin, pseudohypericin, flavonol glycosides, and phloroglucinols, etc, and pure hypericin inhibited T-type calcium channel activity in cultured neuroblastoma cells.

*Hypericum* extracts or extracts of other species of the *Hypericum* genus can be obtained either through commercially available sources or extracted from original whole fresh or dried plant of *Hypericum* or other species of the *Hypericum* genus containing not less than 0.04% naphthodianthrones of the hypericin group calculated as hypericin. *Hypericum* extracts can be easily prepared by organic solvent extraction or supercritical fluid extraction by carbon dioxide (E. Bombardelli and P. Morazzoni, *Fitoterapia*, vol. 66, pp. 43–68, 1995; S. S. Chatterjee et al, *Pharmacopsychiat.*, vol. 31 (Suppl.), pp. 7–15, 1998; W. Dimpfel et al, *Pharmacopsychiat.*, vol. 31 (Suppl.), pp. 30–35, 1998). As an example, 1 kg of finely ground dried *Hypericum perforatum* was stirred with 8 l of 80% ethanol under nitrogen at 55° C. for 1 hour. The mixture was centrifuged under nitrogen and the supernatant was collected. Ascorbic acid (0.1%) was added and the extract was dried under reduced pressure to give a *Hypericum* extract. It is noted that other organic solvents, e.g. alkyl alcohols other than ethanol, acetone, methyl n-butyl ketone, n-hexane, DMSO and toluene, can be used to extract *Hypericum perforatum* to make *Hypericum* extracts. The plant, *Hypericum perforatum*, can be obtained worldwide such as England, China, Holland, French, German, Italy, Russia, Spain and Sweden.

Another embodiment of the present invention includes extracts from species of the *Hypericum* genus other than St. John's Wort or *Hypericum perforatum*, and extracts from other plants containing hypericin, as well as methods of using these extracts in treating health disorders related to T-type calcium channels or treatable with T-calcium channel blockers. Also within the scope of the present invention are methods of using species of the *Hypericum* genus, other than St. John's Wort (*Hypericum perforatum*), or other plants containing hypericin to treat health disorders related to T-type calcium channels or treatable with T-calcium channel blockers.

*Hypericum* extracts usually contain hypericin and various amounts of other chemicals, including pseudohypericin; a broad range of flavonoids, such as quercetin, quercitrin, isoquercitrin, hyperoside, rutin, amentoflavone and hyperin; phloroglucinols, such as hyperforin and ashyperforin; the essential oil; and xanthones. In the present invention, *Hypericum* constituents include hypericin, pseudohypericin, flavonoids, such as quercetin, quercitrin, isoquercitrin, hyperoside, rutin, amentoflavone and hyperin, phloroglucinols, such as hyperforin and ashyperforin, the essential oil from *Hypericum perforatum*, and xanthones. Other embodiments of the present invention are *Hypericum* extract constituents, which include hypericin, pseudohypericin, flavonoids, such as quercetin, quercitrin, isoquercitrin, hyperoside, rutin, amentoflavone and hyperin, phloroglucinols, such as hyperforin and ashyperforin, the essential oil from *Hypericum perforatum*, and xanthones. Also within the scope of the present invention are methods of using *Hypericum* constituents or *Hypericum* extract constituents in treating health disorders related to T-type calcium channels or treatable with T-calcium channel blockers.

A further embodiment of the present invention includes hypericin derivatives and hypericin analogs. Chemicals other than hypericin in Hypericum extract may potentiate the biological effect of hypericin as proved by their synergistic effects of inhibiting T-type calcium channel activity. Also within the scope of the present invention are methods of using hypericin derivatives or hypericin analogs in treating health disorders related to T-type calcium channels or treatable with T-calcium channel blockers.

The term "hypericin analog" refers to compounds having a chemical structure similar to hypericin and having T-type calcium channel blocking activities like hypericin, but

"hypericin analog" excludes Mibefradil. Examples of hypericin analogs include emodin and a compound of formula I shown below.

Emodin

In the present application, hypericin derivatives are compounds modified from hypericin. Pseudohypericin can be considered as a hypericin derivative. Hyperin and hypericin derivatives of the present invention include compounds of formula II shown below.

wherein
$R_1$ is H, OH, OR or OCOR;
$R_2$ is H, R, F, Cl, Br, I or $SO_3H$;
$R_3$ is H, R, OH, OR, OCOR, $CH_2OH$, $CH_2OR$, $CH_2OCOR$, COOH or COOR;
$R_4$ is H, R, OH, OR, OCOR, $CH_2OH$, $CH_2OR$, $CH_2OCOR$, COOH or COOR;
$R_5$ is H, R, F, Cl, Br, I or $SO_3H$;
$R_6$ is H, OH, OR or OCOR;
$R_7$ is H, OH, OR or OCOR;
$R_8$ is H, R, F, Cl, Br, I or $SO_3H$;
$R_9$ is H, R, OH, OR, OCOR, $CH_2OH$, $CH_2OR$, $CH_2OCOR$, COOH or COOR;
$R_{10}$ is H, R, OH, OR, OCOR, $CH_2OH$, $CH_2OR$, $CH_2OCOR$, COOH or COOR;
$R_{11}$ is H, R, F, Cl, Br, I or $SO_3H$;
$R_{12}$ is H, OH, OR or OCOR; and
R is an alkyl or substituted alkyl group.

It is noted that the compound of formula II wherein $R_1$, $R_3$, $R_4$, $R_6$, $R_7$ and $R_{12}$ are OH, $R_2$, $R_5$, $R_8$ and $R_{11}$ are H, and $R_9$ and $R_{10}$ are methyl is hypericin itself. It is also noted that the compound of formula II wherein $R_1$, $R_3$, $R_4$, $R_6$, $R_7$ and $R_{12}$ are OH, $R_2$, $R_5$, $R_8$ and $R_{11}$ are H, $R_9$ is methyl and $R_{10}$ is hydroxymethyl is pseudohypericin.

In the present invention, "alkyl" represents a $C_1$–$C_{30}$ linear or branched saturated or unsaturated hydrocarbyl group. Preferably, "alkyl" is a $C_1$–$C_6$ linear or branched saturated or unsaturated hydrocarbyl group.

The alkyl group of R can be optionally substituted with one to three substituents independently selected from hydroxy, alkoxy, acyloxy, carboxy, akoxycarbonyl, amino, alkylamino, dialkylamino, nitro or phenyl group or fluorine, chlorine, bromine or iodine atom.

Further preferred are compounds of formula II, wherein
$R_1$ is H, OH, OR or OCOR;
$R_2$ is H or R;
$R_3$ is H, OH, OR, OCOR, $CH_2OH$, $CH_2OR$ or $CH_2OCOR$;
$R_4$ is H, OH, OR, OCOR, $CH_2OH$, $CH_2OR$ or $CH_2OCOR$;
$R_5$ is H or R;
$R_6$ is H, OH, OR or OCOR;
$R_7$ is H, OH, OR or OCOR;
$R_8$ is H or R;
$R_9$ is H, OH, OR, OCOR, $CH_2OH$, $CH_2OR$ or $CH_2OCOR$;
$R_{10}$ is H, OH, OR, OCOR, $CH_2OH$, $CH_2OR$ or $CH_2OCOR$;
$R_{11}$ is H or R;
$R_{12}$ is H, OH, OR or OCOR; and
R is an optionally substituted $C_1$–$C_6$ alkyl group, as well as methods of using these compounds to treat health disorders treatable with T-calcium channel blockers.

It is also preferred that R is an optionally substituted methyl or ethyl group.

The hypericin derivatives of the present invention with alkyl or substituted alkyl group(s), i.e. compounds of formula II with alkyl or substituted alkyl group(s) at $R_2$, $R_3$, $R_4$, $R_5$, $R_8$, $R_9$, $R_{10}$, and/or $R_{11}$ position, can be synthesized from appropriately substituted emodin anthones by dimerization (see Y. Mazur et al, CA 2,029,993; H. Falk et al, Monatsh. Chem., vol. 126, pp. 993–1000, 1995; H. Falk and T. N. H. Tran, Monatsh. Chem., vol. 127, pp. 717–723, 1996; R. Altmann et al, Monatsh. Chem., vol. 129, pp. 235–244, 1998; G. A. Kraus and W. Zhang, Bioorg. Med. Chem., vol. 5, pp. 2633–2636, 1995). For example, a hypericin derivative, wherein $R_1$, $R_3$, $R_4$, $R_6$, $R_7$, and $R_{12}$ are OH, $R_2$, $R_5$, $R_8$, and $R_{11}$ are H, and $R_9$ and $R_{10}$ are $C_{19}H_{39}$, was synthesized from anthone of formula I by dimerization in the presence of pyridine N-oxide, piperidine, and ferrous sulfate in pyridine.

O-Substituted hypericin derivatives or hypericin analogs can be synthesized by direct etherification and esterification of the phenolic hydroxyl group of hypericin and/or hypericin analogs (see H. Falk and T. N. H. Tran, Monatsh. Chem., vol. 127, pp. 717–723, 1996; G. A. Kraus and W. Zhang, Bioorg. Med. Chem., vol. 5, pp. 2633–2636, 1995). For example, a hypericin derivative, wherein $R_1$, $R_3$, $R_4$, $R_6$, $R_7$, and $R_{12}$ are OMe, $R_2$, $R_5$, $R_8$, and $R_{11}$ are H, and $R_9$ and $R_{10}$ are methyl, was prepared by methylation of hypericin with dimethyl sulfate under basic condition.

Hypericin derivatives having halogen or sulfonate substitution, i.e. compounds of formula II wherein $R_2$, $R_5$, $R_8$, and/or $R_{11}$ are halogen or SO3H, or halogenated or sulfonated hypericin analogs can be synthesized by direct halogenation or sulfonation of hypericin or hypericin analog (H. Falk and W. Schmitzberger, Monatsh. Chem., vol. 124, pp. 77–81, 1993; H. Falk et al, Monatsh. Chem., vol. 129, pp. 309–318, 1998). For example, a hypericin derivative, wherein $R_2$, $R_5$, $R_8$, and/or $R_{11}$=Br, was prepared by bromination of hypericin in pyridine.

Other hypericin derivatives of formula II can be prepared by derivatization of hypericin, pseudohypericin or the hypericin derivatives described above using processes known in the art. For instance, one or more of the hydroxy groups in hypericin, pseudohypericin or the hypericin derivatives described above can be derivatized by converting the hydroxy group(s) to a protected hydroxy group(s) according to the processes described in T. W. Greene and P. G. M. Wuts, *Protective Groups in Organic Synthesis*, John Wiley & Sons, Inc., New York, 1991, the disclosure of which is incorporated by reference. Similarly, hypericin derivatives can be prepared by converting hypericin or pseudohypericin into a prodrug of hypericin or pseudohypericin using processes known in the art, e.g. the processes described in H. Bundgaard, *Design of Prodrugs*, Elsevier Science Publishers, Amsterdam, 1985, the disclosure of which is incorporated by reference. The present invention includes prodrug forms of the agents disclosed above and methods of using the prod rug forms to treat health disorders related to T-type calcium channels or treatable with T-calcium channel blockers. For instance, hypericin prodrugs, pseudohypericin prodrugs and methods of using hypericin prodrugs or pseudohypericin prodrugs to treat health disorders related to T-type calcium channels or treatable with T-calcium channel blockers are also contemplated in the present invention.

The present invention also provides pharmaceutical compositions comprising *Hypericum*, *Hypericum* extract, a compound found in *Hypericum*, i.e. *Hypericum* constituent, including hypericin, pseudohypericin, hyperforin, ashyperforin, quercetin, quercitrin, isoquercitrin, hyperoside, rutin, amentoflavone and hyperin, hypericin derivatives or hypericin analogs, or an extract of a species of the *Hypericum* genus other than *Hypericum perforatum* admixed with a pharmaceutically acceptable carrier. Also within the scope of the present invention is a pharmaceutical composition comprising at least two *Hypericum* constituents, one of which is preferably hypericin, with or without a pharmaceutically acceptable carrier. It is further preferred that the pharmaceutical composition comprises hypericin and pseudohypericin. It is also preferred that the pharmaceutical composition comprises hypericin and hyperforin. A further aspect of the present invention is a pharmaceutical composition comprising a *Hypericum* constituent and a hypericin derivative or hypericin analog.

Numerous standardized extracts are available yielding from 0.4 to 2.7 mg of hypericin per daily dose. These are prepared in a variety of ways according to the various manufacturers. The extracts are normally standardized by containing 0.24–0.32% total hypericin.

The primary compounds, hypericin and pseudohypericin (naphthodianthrones), are naturally occurring pigments and characteristic markers for *Hypericum* plant and can be extracted in methanol or ethanol. Hypericin and pseudohypericin can also be obtained synthetically by processes known in the art. Synthetic hypericin is also available commercially. Similarly, *Hypericum* extract constituents, such as hypericin, pseudohypericin, flavonoids, phloroglucinols and xanthones, can be obtained by synthetic processes known in the art or by high pressure liquid chromatography of *Hypericum* extracts, followed by work-up procedures known to one skilled in the art.

The present invention also provides methods of using *Hypericum*; *Hypericum* extracts; *Hypericum* constituents, e.g. hypericin, pseudohypericin, flavonoids, such as quercetin, quercitrin, isoquercitrin, hyperoside, rutin, amentoflavone and hyperin, phloroglucinols, such as hyperforin and ashyperforin, the essential oil from *Hypericum perforatum*, and xanthones; hypericin derivatives; hypericin analogs; an extract of a species of the *Hypericum* genus other than *Hypericum perforatum*; or the pharmaceutical compositions disclosed above for treating health disorders related to T-type calcium channels or treatable with T-calcium channel blockers. In these methods, *Hypericum*, *Hypericum* extract, hypericin, pseudohypericin, flavonoids, such as quercetin, quercitrin, isoquercitrin, hyperoside, rutin, amentoflavone and hyperin, phloroglucinols, such as hyperforin and ashyperforin, the essential oil from *Hypericum perforatum*, xanthones, hypericin derivatives, hypericin analogs, an extract of a species of the *Hypericum* genus other than *Hypericum perforatum*; or the pharmaceutical compositions disclosed above may be administered to an animal, e.g. a mammal such as a human, in need of such a treatment by a parenteral, opthalmological, topical, oral or rectal route or by inhalation. Examples of parenteral route are intravenous, subcutaneous and intramuscular routes.

*Hypericum* extract, hypericin, pseudohypericin, flavonoids, such as quercetin, quercitrin, isoquercitrin, hyperoside, rutin, amentoflavone and hyperin, phloroglucinols, such as hyperforin and ashyperforin, the essential oil from *Hypericum perforatum*, and xanthones, hypericin derivatives, or hypericin analogs may be formulated for parenteral, ophthalmological, topical, oral or rectal administration by compounding these active agents with a conventional vehicle, excipient, binder, preservative, stabilizer, dye, flavoring agent, or the like, as called for by accepted pharmaceutical practice.

The doses of the active agents used in the methods of the present invention are described herein. Daily doses are in the range of 0.05 to 500 mg per kg of body weight, prefereably 0.5 to 50 mg per kg of body weight, for *Hypericum* extract, an extract of a species of the genus *Hypericum* other than *Hypericum perforatum*, or an extract of a plant containing hypericin. Daily doses are in the range of 0.0001 to 10 mg per kg of body weight, preferably 0.0015 to 0.15 mg per kg of body weight, for hypericin and 0.001 to 5 mg per kg of body weight for a hypericin derivative, such as pseudohypericin, or hypericin analog. For *Hypericum* extract constituents or *Hypericum* constituents, other than hypericin and pseudohypericin, the daily doses are in the range of 0.01 to 100 mg per kg of body weight, preferably of 0.05 to 50 mg per kg of body weight.

*Hypericum perforatum*, or species of the *Hypericum* genus other than *Hypericum perforatum*, fresh or dried, can be used in the methods of treating health disorders related to T-type calcium channels or treatable with T-calcium channel blockers. In the present invention, "fresh *Hypericum perforatum*" includes the entire plant of *Hypericum perforatum* or a portion of *Hypericum perforatum* plant in a fresh state. In the present invention, "dried *Hypericum pefforatum*" includes the entire plant of *Hypericum perforatum* or a portion of *Hypericum perforatum* plant in a dry state, as well as powder resulting from grinding a dried *Hypericum perforatum* plant or a dried portion of a *Hypericum perforatum* plant. The methods of treatment of the present invention can be performed by administering fresh *Hypericum perforatum* or dried *Hypericum perforatum*. For fresh *Hypericum perforatum*, the daily doses are in the range of 1 to 5000 mg per kg of body weight. For dried Hypericum perforatum, the daily doses range from 0.5 to 2000 mg per kg of body weight.

The actual dose of the active agent used in the method of the present invention to treat a particular subject can be selected from the "daily doses" disclosed above depending on the T-calcium channel activity of the active agent, i.e. *Hypericum perforatum, Hypericum* extracts, extracts of a species of the *Hypericum* genus other than *Hypericum perforatum, Hypericum* constituents, hypericin derivatives or hypericin analogs, used in the treatment, the age, race, sex, species and health condition of the subject to be treated and the type and severity of the health disorder to be treated. If used for acute treatments, the above active agents can be administered at the daily doses disclosed above for no more than one day. If needed, the above active agents can be administered to the subject being treated at the above daily doses repetitively day after day.

The extract or hypericin can also be combined with drugs or any other natural substances known to be effective for treating the condition in question.

The following examples illustrate, but are not intended to limit, the present invention.

EXAMPLE 1

Effect of Hypericin on L-type Calcium Current Activity in Cultured Neuroblastoma Cells.

Mouse neuroblastoma cells (N1E115) were cultured in Dulbecco's modified Eagle's medium (GIBCO) containing 10% fetal bovine serum at 37° C. in a humidified atmosphere of 5% $CO_2$ in air. The medium was changed every 3–4 days. After mechanical agitation, $3 \times 10^4$ cells were replanted in 35 mm tissue culture dishes containing 4 ml of bath solution. After cell attachment, the dish was mounted on the stage of an inverted phase-contrast microscope (Nikon) for $Ca^{2+}$ channel current recording. These cells expressed predominately T channel currents. In experiments where L channels were specifically sought, the cells were grown and maintained at confluence for 3–4 weeks under the same culture conditions with the addition of 2% (vol/vol) dimethyl sulfoxide. Three to five days before use, the cells were replanted with the same medium. These cells expressed predominately L channel currents. A small number of these cells also expressed T channel currents. Hence, cells were selected so that at a holding potential of −40 mV, the T channel component was very small and the inward current measured was conducted predominantly by L channels.

The whole-cell version of the patch-clamp technique was used. The pipettes had resistance of 2–15 M. Membrane current recordings were made with an Axopatch-1C (Axon Instruments) patch-clamp amplifier. All signals were filtered at 1 kHz and stored in the computer. Since the peak currents measured with 20 mM $Ba^{2+}$ as the charge carrier were usually small (about 200 pA), the series resistance compensation was not usually employed. If the capacitive transient overlapped with the onset of the inward current, or if the spatial voltage control was inadequate (i.e., NIE-115 cells with long neural outgrowths), the experimental data were rejected. Unless otherwise specified the current-voltage plots were constructed by using the peak values (corrected for leakage) from the original records for both T and L channel currents. The holding membrane potential was fixed at −80 mV when the T channels were under investigation or at 40 mV when the L channels were studied. $Ba^{2+}$ currents through $Ca^{2+}$ channels were elicited by 200 msec depolarization at intervals of 5 sec. For every single-cell recording, stable readings were first obtained for 5 min; the drug was then added to the bath solution. Experiments were performed at room temperature(21–22° C.) to prolong cell survival and channel recording time. The bath solution contained 110 mM Tris, 5 mM KCL, 5 mM CsCL, 20 mM Hepes, 30 mM glucose, 20 mM $BaCL_2$, and 0.5 M tetrodotoxin. The pipette (internal) solution contained 70 mM $Cs_2$-aspartame, EGTA 10, 2 mM ATP-$Na_2$, 5 mM K-pyruvate, 5 mM K-succinate, 5 mM Phosphocreatine-$Na_2$, 15 units/ml Creatine kinase, Hepes and 5 mM glucose. The osmolarity of all solutions was adjusted to 310–320 mOsm and pH to 7.4 using HCL or CsOH as required.

Figure 1:
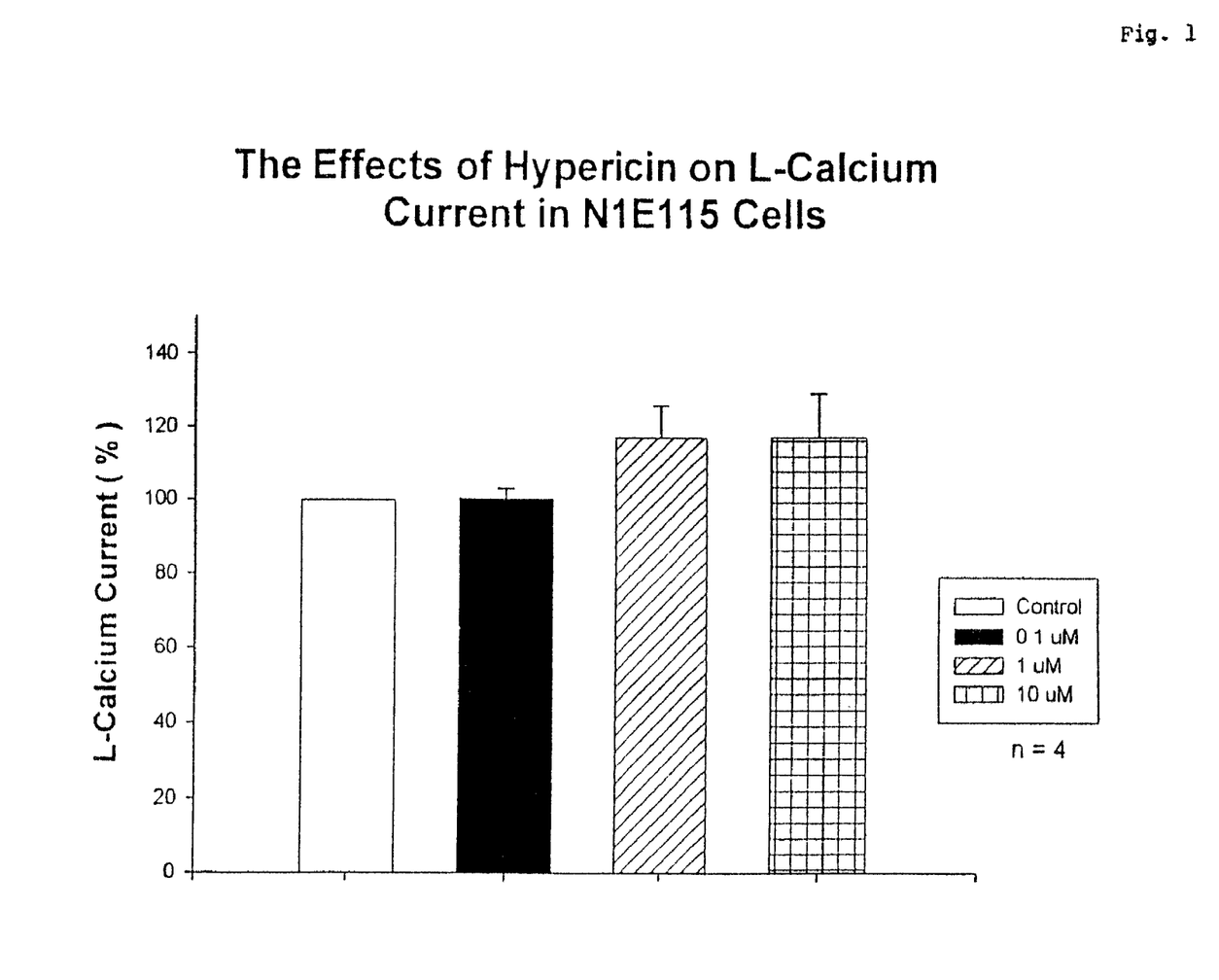
FIG. 1 shows the effect of hypericin on L-type calcium current activity in cultured N1E-115 cells. At doses of 0.1, 1 and 10 uM, hypericin causes a slight but not significant increase in L-type calcium currents.
Figure 2:
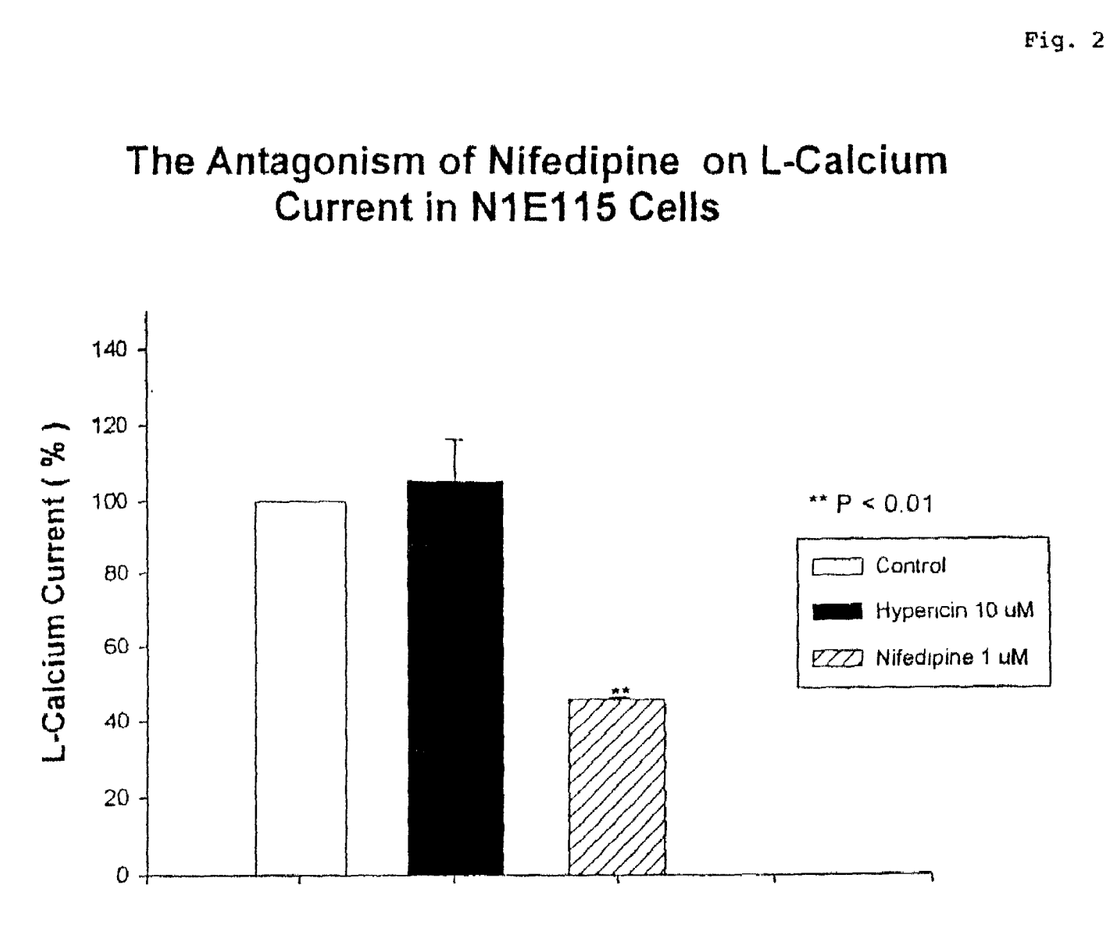
FIG. 2. Shows the effect of nifedipine on L-type calcium current activity in cultured N1E-115 cells. The cells were added into nifedipine after not responding to hypericin (10 uM). 1 uM of nifedipine significantly inhibited the currents, indicating the existence of L-type calcium channels.

FIG. 1 shows that hypericin does not significantly affect L-type calcium current. FIG. 2 shows that Nifedipine, a known L-type calcium channel blocker significantly inhibits L-type calcium currents.

EXAMPLE 2

Effect of Hypericin on T-type Calcium Currents in N1E-115 Cells.

Figure 3:
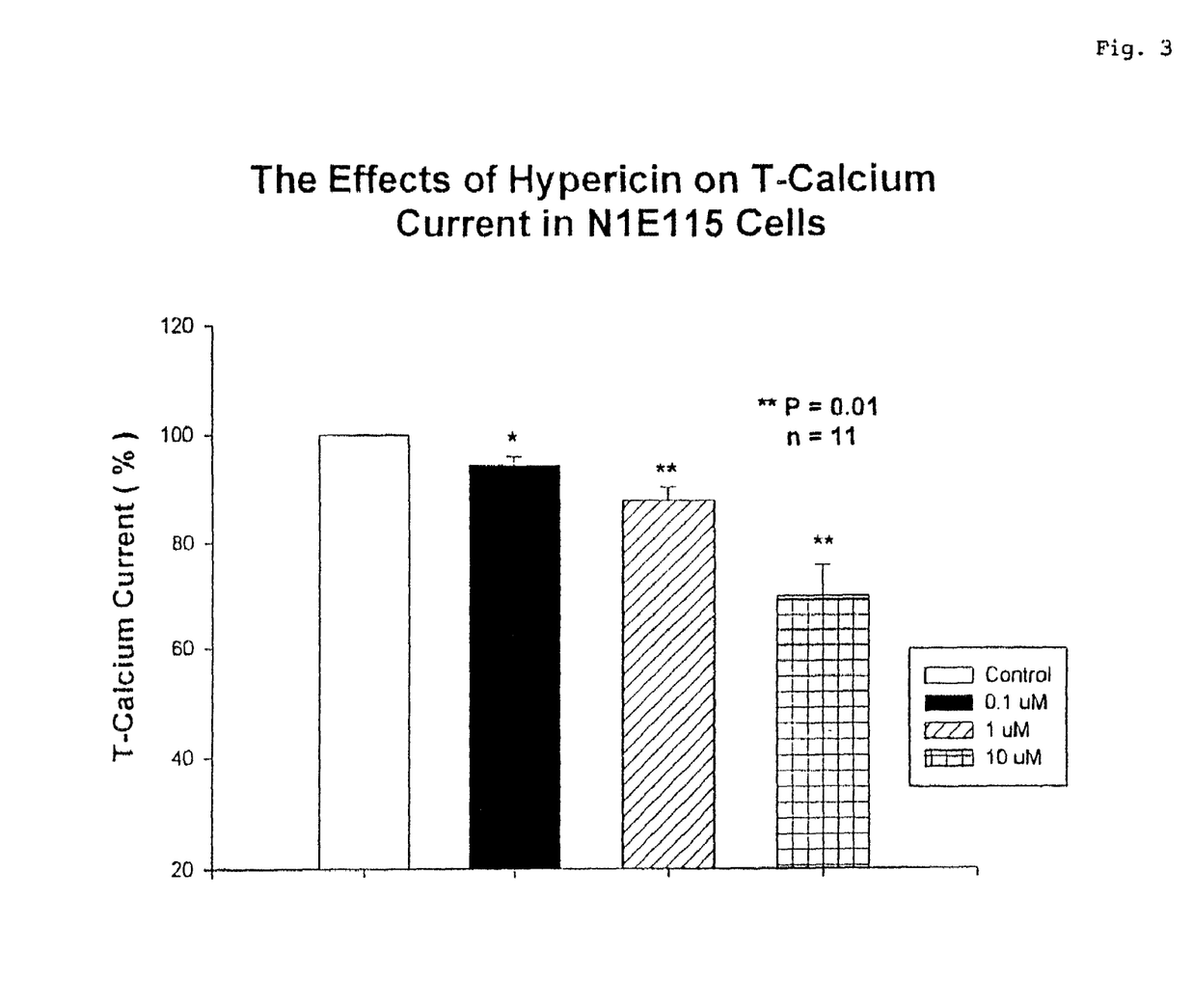
FIG. 3 shows the effect of hypericin on T-type calcium current in N1E-115 cells. Hypericin causes a dose-dependent inhibitory effect on T-type calcium current from 0.1 to 10 uM.
Figure 4:
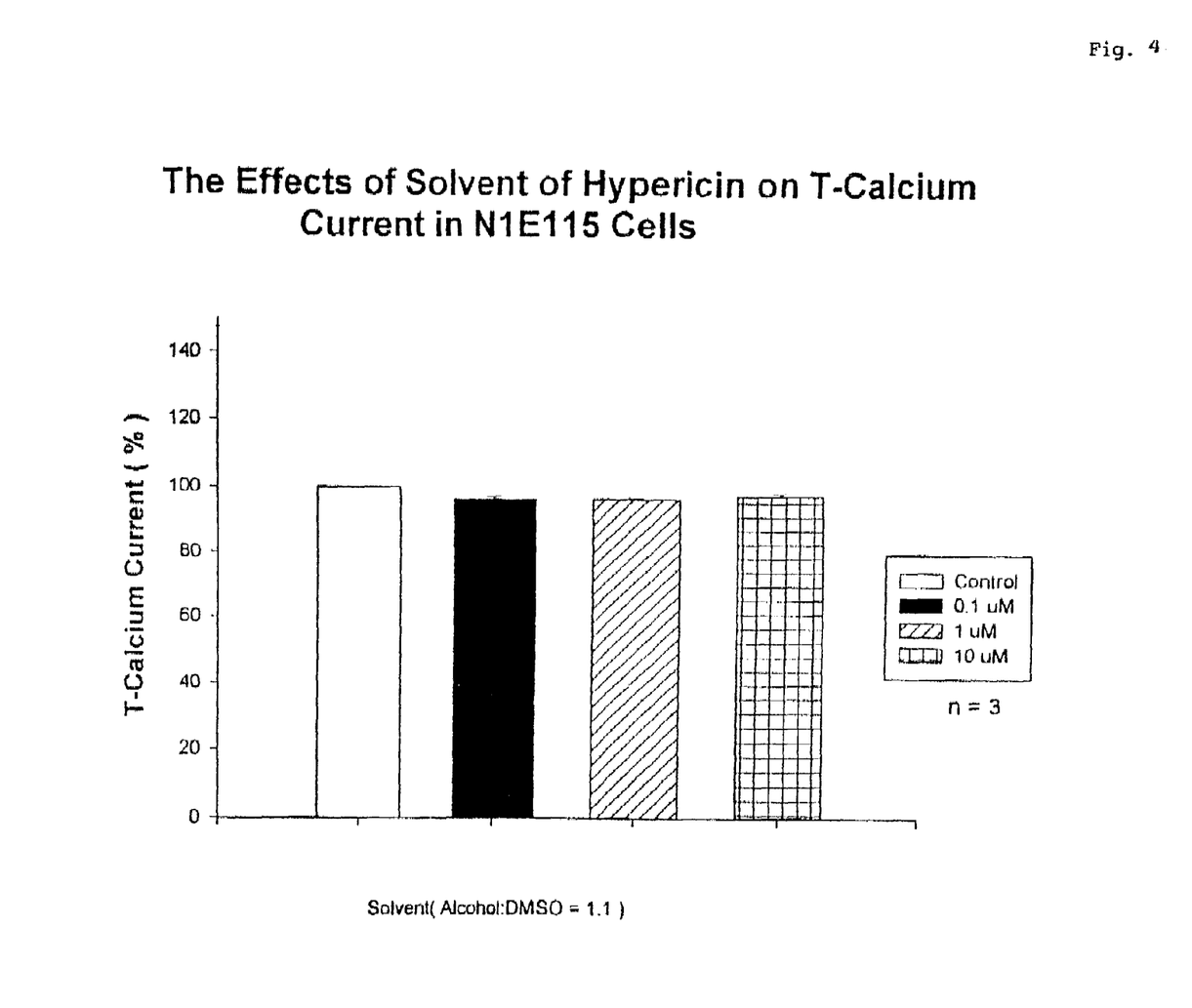
FIG. 4 shows the effect of solvent control for hypericin on T-type calcium channel activity. Since hypericin is dissolved in a solvent of ethanol (50%)+DMSO (50%). This solvent is tested for its effect on T-type current. In the amount equivalent to dissolving 0.1 to 10 uM of hypericin, this control solvent does not affect T-type calcium currents.

The method is described as above (Example 1). FIG. 3 shows that hypericin inhibited T-type calcium currents in a dose-dependent manner. FIG. 4 shows that the solvent controls did not affect the T-type calcium currents.

EXAMPLE 3

Effect of St. John's Wort Extract (*Hypericum* Extract) on T-type Calcium Current in N1E-115 Cells.

Figure 5:
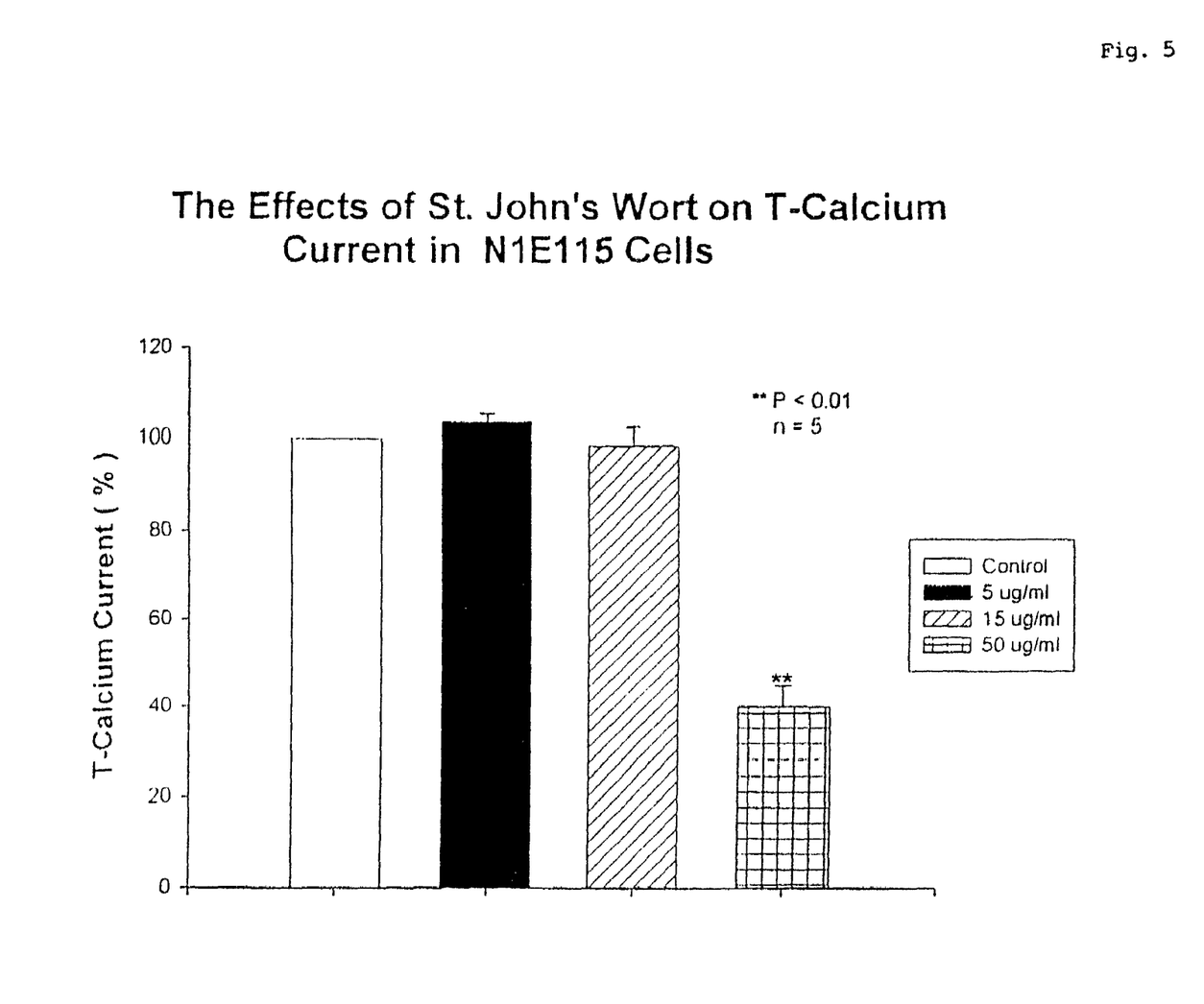
FIG. 5 shows the effect of *Hypericum* extract on T-type calcium current. *Hypericum* extract contains about 0.3% of hypericin and is dissolved in external solution. At 50 ug/ml, *Hypericum* extract significantly inhibited T-type calcium channel currents.

The method is described as above (Example 1). *Hypericum* extract is standardized with about 0.3% of hypericin. As shown in FIG. 5, at, 50 ug/ml, *Hypericum* extract containing about 0.15 ug/ml of hypericin significantly inhibited T-type calcium current by more than 60%. However, 0.15 ug/ml of pure hypericin, as shown in FIG. 3 produces less than 10% of inhibition on T-type calcium current. This results suggested that the chemicals other than hypericin in *Hypericum* extract cause a synergistic effect to hypericin on T-type calcium channel activity.

EXAMPLE 4

Effect of Hypericin on L-type Calcium Current in VSMC

Figure 6:
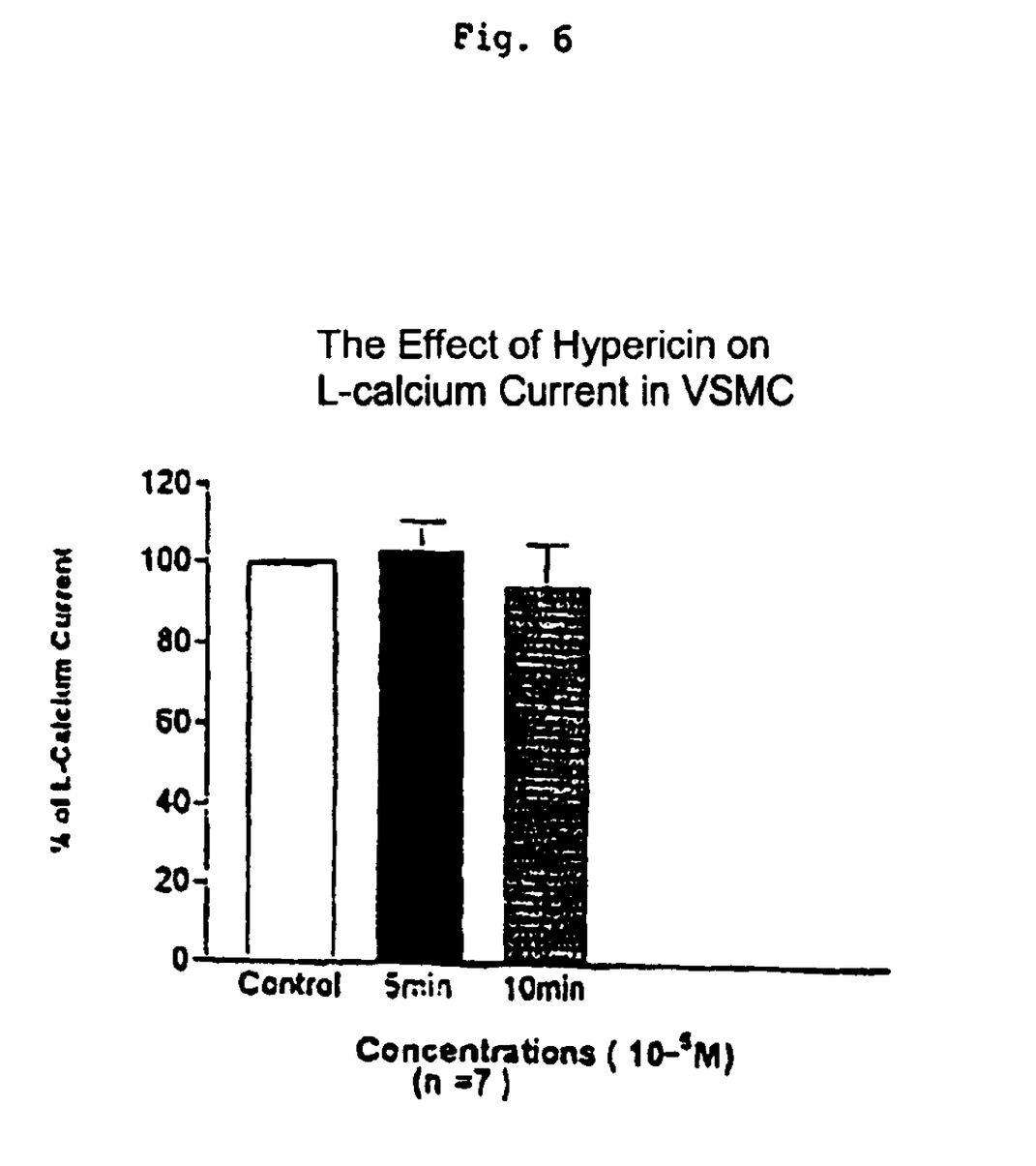
FIG. 6 shows the effect of hypericin on L-type calcium current in vascular smooth muscle cells.

The method is similar to the method described above for Example 1, except that vascular smooth muscle cells (VSMC) were used. As shown in FIG. 6, hypericin did not affect the L-type calcium current in vascular smooth muscle cells.

EXAMPLE 5

Effect of Hypericin on L-type Calcium Current in Ventricular Cells

Figure 7:
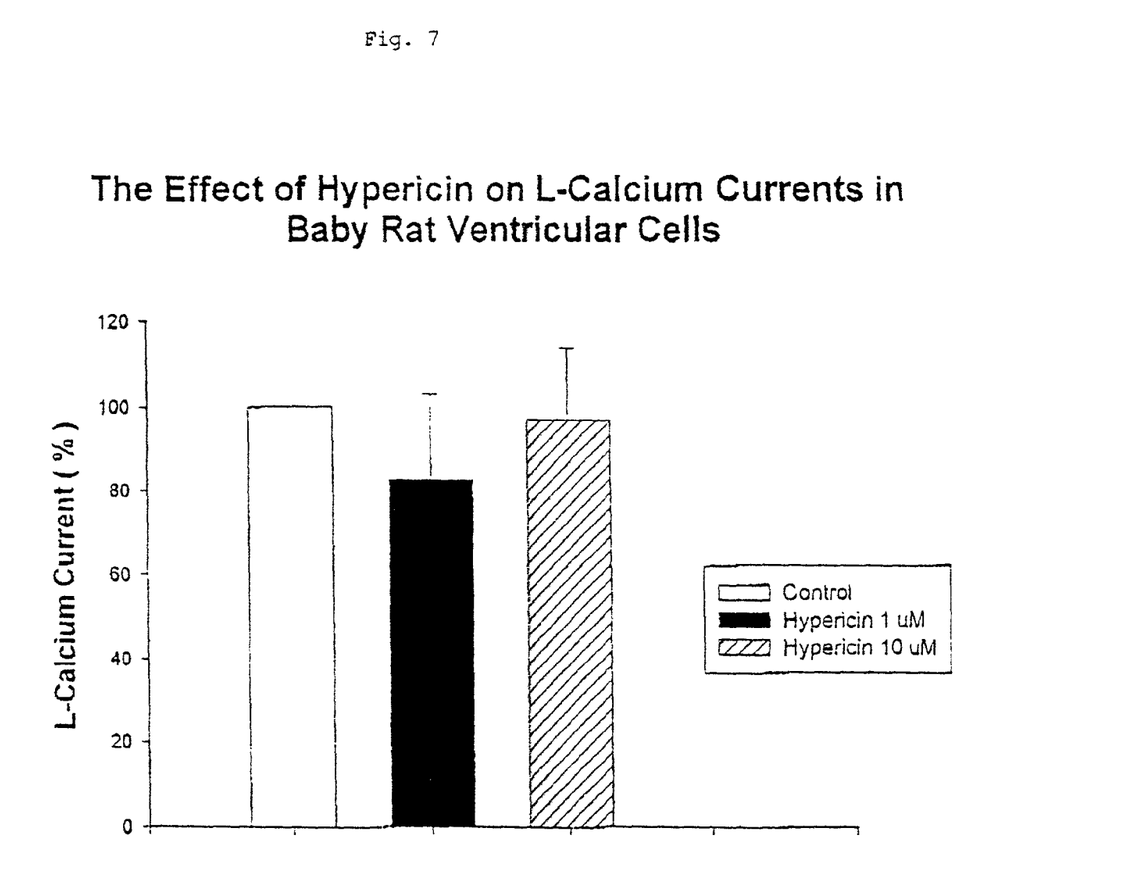
FIG. 7 shows the effect of hypericin on L-type calcium current in ventricular cells from baby rats.

The method is similar to the method described above for Example 1, except that ventricular cells from baby rats were used. As shown in FIG. 7, hypericin did not affect the L-type calcium current in ventricular cells.

What is claimed is:

1. A method of treating a patient by inhibiting T-type calcium channels in a patient's cells, wherein said patient is suffering from chronic heart failure, congestive heart failure, ischemic condition, arrythmia, hypoinsulinemia, hyperinsulinemia, hyperaldosteronemia, epilepsy or preterm labor, comprising administering to said patient a composition comprising a pharmaceutically effective amount of an extract of *Hypericum perforatum* effective to inhibit the movement of calcium ions into cells and a pharmaceutically acceptable carrier.

2. The method according to claim 1, wherein said patient is a human.

3. The method of claim 1, wherein said pharmaceutically effective amount is about 0.05 mg to 500 mg per kg body weight of said patient.

4. The method of claim 1, wherein said extract of *Hypericum* is a methanol or ethanol extract of *Hypericum perforatum*.

5. The method of claim 1, wherein the patient has chronic heart failure.

6. The method of claim 1, wherein said patient has congestive heart failure.

7. The method of claim 1, wherein said health disorder is ischemic condition.

8. The method of claim 1, wherein said patient has arrhythmia.

9. The method of claim 1, wherein said patient has hypoinsulinemia.

10. The method of claim 1, wherein said patient has hyperinsulinemia.

11. The method of claim 1, wherein said patient has hyperaldosteronemia.

12. The method of claim 1, wherein said health disorder is epilepsy.

13. The method of claim 1, wherein said patient has preterm labor.

14. A method according to claim 1, wherein one or more components of said extract other than hypericin contribute to the inhibition of the T-cell calcium current.

15. The method of claim 1, wherein said composition consists essentially of a pharmaceutically effective amount of an extract of *Hypericum perforatum*.

16. The method of claim 1, wherein said pharmaceutically effective amount is about 0.5 mg to 50 mg per kg body weight of said patient.

* * * * *